United States Patent [19]

Koenig et al.

[11] 4,137,261

[45] Jan. 30, 1979

[54] MANUFACTURE OF N-VINYL-N-ALKYL-CARBAMIC ACID CHLORIDES

[75] Inventors: Karl-Heinz Koenig, Frankenthal; Christian Reitel, Heidelberg; Dietrich Mangold, Neckargemuend, all of Fed. Rep. of Germany

[73] Assignee: BASF Aktiengesellschaft, Ludwigshafen, Fed. Rep. of Germany

[21] Appl. No.: 754,598

[22] Filed: Dec. 27, 1976

[30] Foreign Application Priority Data

Jan. 16, 1976 [DE] Fed. Rep. of Germany ....... 2601542

[51] Int. Cl.$^2$ ............................................. C07C 125/03
[52] U.S. Cl. .......................... 260/544 C; 260/544 K
[58] Field of Search ....................... 260/544 C, 544 K

[56] References Cited

U.S. PATENT DOCUMENTS

| | | | |
|---|---|---|---|
| 3,870,707 | 3/1975 | Somlo | 260/544 C |
| 4,001,318 | 1/1977 | Botta | 260/544 C |
| 4,038,311 | 7/1977 | Kiefer et al. | 260/544 C |

FOREIGN PATENT DOCUMENTS

| | | |
|---|---|---|
| 2054660 | 5/1972 | Fed. Rep. of Germany. |
| 2146069 | 3/1973 | Fed. Rep. of Germany ....... 260/544 C |

OTHER PUBLICATIONS

"Rec. Trav. Chim. Pays–Bas," 79 (1960), 1:197 et seq.

*Primary Examiner*—Norman Morgenstern
*Attorney, Agent, or Firm*—Keil, Thompson & Shurtleff

[57] ABSTRACT

N-Vinyl-N-alkyl-carbamic acid chlorides are manufactured by reacting crude Schiff bases, which have advantageously been manufactured in the presence of pentane, with phosgene and tertiary amines, treating the reaction mixture with water and then isolating the end product, after having separated off the aqueous phase containing the amine salt. The products are starting materials for the manufacture of surface-coating intermediates, plastics, paints and crop protection agents.

10 Claims, No Drawings

MANUFACTURE OF N-VINYL-N-ALKYL-CARBAMIC ACID CHLORIDES

The present invention relates to a process for the manufacture of N-vinyl-N-alkyl-carbamic acid chlorides by reacting crude Schiff bases, which have advantageously been manufactured in the presence of pentane, with phosgene and tertiary amines, treating the reaction mixture with water and then isolating the end product, after having separated off the aqueous phase containing the amine salt.

Rec. Trav. Chim. Pays-Bas, 79 (1960), 1,197 et seq. discloses that organic acid chlorides can undergo an addition reaction with N-propylpropanaldimine to give the corresponding N-(1-chloropropyl)-N-propyl-acid amides. On treatment with triethylamine, these adducts lose hydrogen chloride and are converted to the corresponding N-(1-propenyl)-N-propyl-acid amides. After the reaction, the triethylamine hydrochloride formed is filtered off and the filtrate is distilled in order to isolate the end product. Similarly, German Laid-Open Application DOS No. 1,901,542 teaches, in connection with the reaction of Schiff bases with phosgene, and German Laid-Open Application DOS No. 2,054,660 teaches, in connection with the reaction of imide-acid esters with phosgene in the presence of tertiary amines, that when working up the carbamic acid chloride, the amine hydrochloride formed should first be removed from the reaction mixture by filtration. All the examples in both the above applications show this method, involving filtering off the salt. According to the teaching of both the said publications, the filter residue must be washed with organic solvents and the resulting filtrates must be combined with the filtrate from the reaction mixture and worked up by distillation. All these processes are unsatisfactory from the point of view of simple, economical and trouble-free operation and good yield of end product.

Houben-Weyl, Methoden der Organischen Chemie, volume XI/2, page 78 discloses condensing tertiary butylamine and formaldehyde to give the Schiff base, separating off the organic phase of the reaction mixture and drying it over potassium hydroxide, and then distilling the organic phase. Because the Schiff base is readily soluble in water, separating off the water of reaction formed proves difficult and involved, and if the separation is inadequate the yield of end product is greatly reduced.

We have found that N-vinyl-N-alkyl-carbamic acid chlorides of the formula

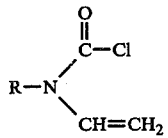

I where R is isopropyl, isobutyl, tertiary amyl or tertiary butyl, are obtained in an advantageous manner by reacting Schiff bases of the formula $$R-N=CH-CH_3 \qquad II$$

where R has the above meanings, with phosgene in the presence of tertiary amines and separating off the end product I, if, after the reaction, the reaction mixture is treated with water, the aqueous phase thus formed and the tertiary amine salts contained therein are separated off and the end product is isolated from the organic phase in the conventional manner.

Further, we have found that the process as claimed in claim 1 can be carried out advantageously by reacting alkylamines of the formula $$R-NH_2 \qquad III$$

where R is isopropyl, isobutyl, tertiary amyl or tertiary butyl, with acetaldehyde in the presence of n-pentane to give the Schiff bases of the formula $$R-N=CH-CH_3 \qquad II$$

where R has the above meanings, separating off all or part of the water formed, reacting the residue with phosgene in the presence of tertiary amines, treating the reacting mixture, after the reaction, with water, separating off the aqueous phase thus formed, and the tertiary amine salts contained therein, and isolating the end product from the organic phase in the conventional manner.

If N-tert.-butylamine, the Schiff base of acetaldehyde and the same amine, and dimethylcyclohexylamine as the tertiary amine, are used, the reaction can be represented by the following equations:

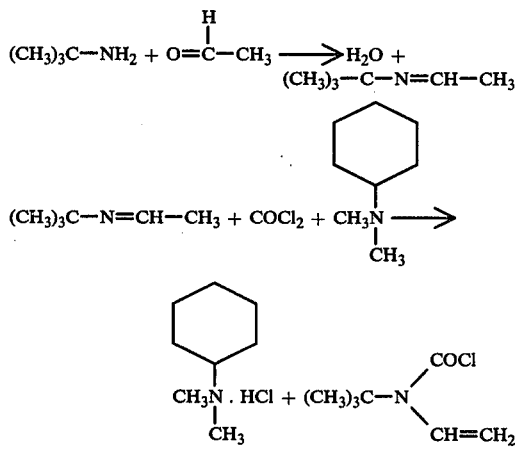

Compared to the prior art, the process of the invention surprisingly gives N-vinyl-N-alkyl-carbamic acid chlorides by a simple method, in some cases with improved yield, with improved space-time yield and in greater purity. Further advantages of the process are that it dispenses with repeated filtration of the reaction mixture and washing of the hydrochloride filtered off, and replaces these involved working-up operations by a simple treatment with water. The water added forms the aqueous phase of the reaction mixture, which takes up the hydrochloride formed and can easily be separated off. Distillation of the organic phase is also simpler and more economical than in the case of conventional processes, since the substantial amounts of solvent used to wash the filter residue are not needed in the new process. In view of the reduction in the amount of solvent used, the process according to the invention is also safer, more reliable and more economical, and causes less pollution of the environment. Using the new method, only liquid phases are produced, which can be handled conveniently by means of pumps. Subsequent neutralization of the aqueous phase permits recovery of the tertiary amine. Accordingly, the process of the invention offers great advantages, particularly for continuous industrial operation. It is surprising that the treatment with water does not produce significant hydrolysis of the end product and accordingly does not detract from the yield.

If n-pentane is used to manufacture the Schiff base, a 2-phase reaction mixture is formed, the aqueous phase of which contains the greater part of the water of reaction and can easily be separated off. n-Pentane advantageously facilitates and assists the formation of the 2-phases and the azeotropic removal of the water of reaction. Surprisingly, the residual water, remaining in the organic phase after the phase separation, is removed with the first fraction of pentane on subsequent distillation. A further advantage is that the Schiff base does not have to be isolated from the reaction mixture and purified. For example, it is possible to separate off only the aqueous layer, or the whole of the water of reaction and only a part of the pentane, or all of the water and pentane, and then to subject the remaining mixture directly to the reaction according to the invention, with phosgene and tertiary amine. This method increases the simplicity and economy of the process, particularly in continuous industrial operation. All these advantages of the process of the invention are surprising in view of the prior art.

Preferred starting materials II and III and accordingly preferred end products I are those where R is tertiary butyl. The starting material II can be reacted with stoichiometric amounts of phosgene or with an excess of the latter, e.g. using a ratio of from 1 to 1.2 moles of phosgene per mole of starting material II. The reaction is carried out in the presence of a tertiary amine which is advantageously used in an amount of from 1 to 1.5 moles per mole of starting material II. Suitable tertiary amines are those of the formula

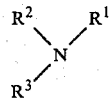    IV where $R^1$, $R^2$ and $R^3$ are identical or different and each is a cycloaliphatic radical, advantageously cycloalkyl of 5 to 8 carbon atoms, an araliphatic radical, advantageously aralkyl of 7 to 12 carbon atoms, an aromatic radical, advantageously phenyl, or, preferably, an aliphatic radical, advantageously alkyl of 1 to 7 carbon atoms, and furthermore $R^1$ and $R^2$, or $R^1$, $R_2$ and $R^3$, together with the adjacent nitrogen, may advantageously be members of a heterocyclic ring. Preferred heterocyclic rings are those with 5 or 6 members, which in addition to the nitrogen may also contain an oxygen atom. The above radicals and rings may furthermore be substituted by groups which are inert under the reaction conditions, e.g. alkyl of 1 to 4 carbon atoms.

Advantageous amines to use are trimethylamine, triethylamine, tri-n-propylamine, triisopropylamine, tri-n-butylamine, triisobutylamine, tri-sec.-butylamine, tri-tert.-butylamine, tripentylamine, tripentyl-(2)-amine, tripentyl-(3)-amine, tri-n-hexylamine, di-(methyl)-cyclohexylamine, di-(ethyl)-cyclohexylamine, di-(n-propyl)-cyclohexylamine, di-(isopropyl)-cyclohexylamine, di-(n-butyl)-cyclohexylamine, di-(isobutyl)-cyclohexylamine, di-(sec.-butyl)-cyclohexylamine, di-(tert.-butyl)-cyclohexylamine and corresponding N,N-disubstituted anilines, benzylamines and o-, m- and p-toluidines; similarly N-mono-substituted pyrrolidine, pyrazolidine, imidazolidine, hexamethyleneimine, piperidine and morpholine; 2-methylpyridine, 3-methylpyridine, 4-methylpyridine, 2,4-dimethylpyridine, 2,6-dimethylpyridine, 2,4,6-trimethylpyridine and especially pyridine; pyridazine, pyrimidine and pyrazine; and corresponding amines containing 3 of the above radicals, of which, however, some or all are different from one another, e.g. N,N-dimethylaniline, N-methyl-N,N-diethylamine and N-methyl-N-ethyl-N-n-propylamine.

The reaction is advantageously carried out at from $-30°$ to $+150°$ C., preferably from 0° to 110° C., under atmospheric or superatmospheric pressure, and continuously or batchwise. Organic solvents which are inert under the reaction conditions may or may not be used; examples of such solvents are aromatic hydrocarbons, e.g. toluene, ethylbenzene, o-, m- and p-xylene, isopropylbenzene and methylnaphthalene; halohydrocarbons, especially chlorohydrocarbons, e.g. tetrachloroethylene, 1,1,2,2- or 1,1,1,2-tetrachloroethane, cyclohexyl chloride, dichloropropane, methylene chloride, dichlorobutane, isopropyl bromide, n-propyl bromide, butyl bromide, chloroform, chloronaphthalene, dichloronaphthalene, carbon tetrachloride, 1,1,1- or 1,1,2-trichloroethane, trichloroethylene, pentachloroethane, 1,2-dichloroethane, 1,1-dichloroethane, n-propyl chloride, 1,2-cis-dichloroethylene, n-butyl chloride, 2-, 3- and iso-butyl chloride, chlorobenzene, o-, p- and m-dichlorobenzene, o-, p- and m-dibromobenzene, o-, m- and p-chlorotoluene, 1,2,4-trichlorobenzene, 1,10-dibromodecane and 1,4-dibromobutane, numerous ethers, e.g. ethyl propyl ether, methyl tert.-butyl ether, n-butyl ethyl ether, di-n-butyl ether, diisobutyl ether, diisoamyl ether, diisopropyl ether, anisole, phenetole, cyclohexyl methyl ether, diethyl ether, tetrahydrofuran and $\beta,\beta$-dichlorodiethyl ether, and mixtures of the above. The solvent is advantageously used in an amount of from 50 to 10,000 percent by weight, preferably from 100 to 500 percent by weight, based on starting material II.

The reaction may be carried out as follows: phosgene is passed into the starting material II, mixed with amine and solvent, for from 1 to 3 hours at the reaction temperature. It is also possible to mix the phosgene with the solvent and add amine and starting material II, with or without solvent, to the mixture. After addition of all the components, the mixture is advantageously stirred for from 0.5 to 4 hours. Unconverted phosgene is then removed from the mixture, e.g. by passing a stream of nitrogen into the mixture. Water is now added, preferably in an amount of from 50 to 500 percent by weight, especially from 50 to 100 percent by weight, based on the reaction mixture. The treatment of the reaction mixture with water is advantageously carried out with thorough mixing, at from $-20°$ to $+50°$ C., preferably from $-10°$ to $+20°$ C., especially from $-5°$ to $+5°$ C., under atmospheric or superatmospheric pressure, continuously or batchwise, for from 1 to 20 minutes. The aqueous phase, which contains from 98 to 100 percent by weight of the hydrochloride formed, is then removed from the 2-phase mixture formed, and the end product is isolated from the organic phase in the conventional manner, e.g. by distillation. The amine can advantageously be recovered from the aqueous phase by adding inorganic bases, advantageously alkaline compounds, e.g. sodium hydroxide solution, and by distillation and be re-used.

In a further advantageous embodiment, the Schiff base II is first prepared from the alkylamine and a stoichiometric amount or excess of the acetaldehyde, e.g. using a ratio of from 1 to 1.5 moles of acetaldehyde per mole of starting material III, in a mixture with pentane. The preparation is advantageously carried out for from 15 to 300 minutes at from −10° to +50° C., preferably from 10° to 15° C., under atmospheric or superatmospheric pressure, continuously or batchwise; it is advantageous to use from 50 to 1,000, preferably from 100 to 200, percent by weight of pentane, based on starting material III. The aqueous phase formed, which as a rule contains from 80 to 95 percent by weight of the total water of reaction formed, is then advantageously separated off, and the organic phase is distilled. On distillation, the remaining water of reaction (from 5 to 20 percent by weight) passes over with the first fraction of from 5 to 50 percent by weight of the total amount of n-pentane.

The crude end product remaining as the residue is directly used further, for the phosgenation according to the invention. Another advantageous method is to separate off the aqueous phase and only distil off sufficient pentane to remove all the water of reaction, after which the remaining mixture is passed to the phosgenation stage. When isolating the end product, residual water in the organic phase of the reaction mixture is thus advantageously distilled off as an azeotrope with n-pentane (the boiling point of the azeotrope being 34.6° C.).

The compounds which may be manufactured by the process of the invention are valuable starting materials for the manufacture of surface-coating raw materials, plastics, paints and crop protection agents. Thus, for example, they can be used to manufacture, by reaction with arylamines, the N-(1-alkenyl)-ureas described as phytotoxic agents in Belgian Patent No. 702,425. They can also be copolymerized with other monomers, e.g. acrylic and methacrylic esters and styrene. For details of the copolymerization, reference may be made to Houben-Weyl, Methoden der Organischen Chemie, volume 14/1, page 24 (1961). The copolymers may be used as coatings or films on building materials, e.g. wooden, stone or concrete surfaces. Such coatings or films may be produced in any desired manner, using conventional methods (Ullmanns Encyklopädie der technischen Chemie, volume 11, pages 283 and 367 et seq. (1960)). Crosslinking agents for polyamines can also be manufactured by polymerizing the end products I. The crosslinking of the polyamines is carried out, for example, in accordance with the processes described in the above volume of Houben-Weyl. The pyrolysis of the end products I, e.g. using the process described in German Pat. No. 1,922,412, gives 1-alkenyl isocyanates, e.g. vinyl isocyanate, which are valuable monomers or comonomers for polymeric materials. Regarding the use of the products, reference may furthermore be made to German Pat. No. 1,901,542, cited in discussing the prior art.

In the Examples which follow, parts are by weight.

EXAMPLE 1

60 parts of phosgene are introduced into 224 parts of methylene chloride. 39.6 parts of ethylidene-tert.-butylamine, 51 parts of dimethylcyclohexylamine and 210 parts of methylene chloride are added to this solution in the course of one hour at from 0° to 5° C., whilst stirring. The mixture is then stirred for 30 minutes, after which the reaction solution is freed from excess phosgene. The mixture is now thoroughly mixed with 250 parts of water at 0° C., whereupon the dimethylcyclohexylamine hydrochloride passes into the aqueous phase. This aqueous phase is separated off and neutralized with sodium hydroxide solution, and the dimethylcyclohexylamine is recovered by distillation. The organic phase is distilled. 52 parts of N-vinyl-N-tert.-butylcarbamoyl chloride (80% of theory) boiling at 85° C./14 mm Hg are obtained.

EXAMPLE 2

627 parts of tert.-butylamine are introduced into 532 parts of n-pentane. A solution of 264 parts of n-pentane and 415 parts of acetaldehyde is stirred into this mixture in the course of 2 hours, at an internal temperature of from 15° to 20° C. The water (155 parts) formed in the reaction separates out as a lower phase and is separated off. The organic phase (azeotropic water/pentane mixture) is then distilled off. A residue comprising 760 parts of the dry Schiff base (90% of theory) is obtained.

The reaction of the Schiff base with phosgene is now carried out by the method described in Example 1. The same yield of end product is obtained.

EXAMPLE 3

(a) 348 parts of tert.-amylamine are introduced into 350 parts of n-pentane. 212 parts of acetaldehyde are stirred into this mixture in the course of 1.5 hours at an internal temperature of from 10° to 15° C.

95 percent by weight of the water (72 parts) formed in the reaction separate out as a second phase and are separated off.

The remaining water (3.6 parts) is removed as an azeotropic water/pentane mixture by partial distillation of the organic phase (removal of 250 parts of n-pentane).

An anhydrous mixture of 100 parts of n-pentane and 408 parts of the Schiff base (91% of theory) are obtained.

(b) 60 parts of phosgene are introduced into 220 parts of methylene chloride. A solution consisting of 44.5 parts of ethylidene-tert.-amylamine, 100 parts of n-pentane, 51 parts of dimethylcyclohexylamine and 210 parts of methylene chloride is added to this mixture in the course of one hour at 0° C., whilst stirring. The reaction solution is stirred for a further 30 minutes and is then freed from excess phosgene.

The mixture is then thoroughly mixed with 250 parts of water at 0° C., whereupon the dimethylcyclohexylamine hydrochloride passes into the aqueous phase. This phase is separated off and neutralized with sodium hydroxide, and the dimethylcyclohexylamine is recovered by distillation.

The organic phase is distilled. 60 parts of N-vinyl-N-tert.-amylcarbamic acid chloride (85% of theory), boiling at 59° C./0.3 mm Hg, are obtained.

We claim:

1. A process for the manufacture of N-vinyl-N-alkylcarbamic acid chlorides of the formula

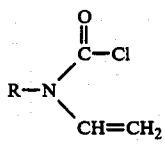

where R is isopropyl, isobutyl, tertiary amyl or tertiary butyl, by reacting Schiff bases of the formula

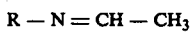

where R has the above meanings, with phosgene in the presence of tertiary amines and separating off the end product I, wherein, after the reaction, excess phosgene is removed and the reaction mixture is treated with water, the aqueous phase thus formed, and the tertiary amine salts contained therein, are separated off and the end product is then isolated from the organic phase in the conventional manner.

2. A process as claimed in claim 1, wherein alkylamines of the formula

where R is isopropyl, isobutyl, tertiary amyl or tertiary butyl, are reacted with acetaldehyde in the presence of n-pentane to give the Schiff bases of the formula

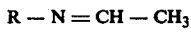

where R has the above meanings, all or part of the water formed is separated off, the residue is then reacted with phosgene in the presence of tertiary amines, the reaction mixture, after the reaction, is treated with water, the aqueous phase thus formed, and the tertiary amine salts contained therein, are separated off and the end product is then isolated from the organic phase in the conventional manner.

3. A process as claimed in claim 1, wherein the reaction is carried out with a ratio of from 1 to 1.2 moles of phosgene per mole of starting material II.

4. A process as claimed in claim 1, wherein the reaction is carried out with from 1 to 1.5 moles of tertiary amine per mole of starting material II.

5. A process as claimed in claim 1, wherein the reaction is carried out at from $-30°$ to $+150°$ C.

6. A process as claimed in claim 1, wherein the reaction is carried out with organic solvents which are inert under the reaction conditions, using from 50 to 10,000 percent by weight of the solvents, based on starting material II.

7. A process as claimed in claim 1, wherein the treatment is carried out at from $-20°$ to $+50°$ C.

8. A process as claimed in claim 1, wherein the treatment is carried out with water, using an amount of from 50 to 500 percent by weight, based on the reaction mixture.

9. A process as claimed in claim 1, wherein the treatment is carried out with from 50 to 1,000 percent by weight of pentane, based on starting material III.

10. A process as claimed in claim 1, wherein the reaction is carried out at from $0°$ to $110°$ C.

* * * * *